US008556085B2

(12) United States Patent
Bogle

(10) Patent No.: US 8,556,085 B2
(45) Date of Patent: Oct. 15, 2013

(54) ANTI-VIRAL DEVICE

(76) Inventor: Stuart Bogle, Wichita, KS (US)

(*) Notice: Subject to any disclaimer, the term of this patent is extended or adjusted under 35 U.S.C. 154(b) by 65 days.

(21) Appl. No.: 12/941,137

(22) Filed: Nov. 8, 2010

(65) Prior Publication Data
US 2012/0111789 A1 May 10, 2012

(51) Int. Cl.
B01D 35/00 (2006.01)
A61F 2/82 (2013.01)

(52) U.S. Cl.
USPC .......... 210/348; 210/356; 210/498; 623/1.15; 623/1.18; 623/1.2

(58) Field of Classification Search
USPC ......... 210/232, 233, 345, 348, 335, 356, 418, 210/498, 645, 646; 435/236; 623/1.15, 623/1.18, 1.2, 1.24
See application file for complete search history.

(56) References Cited

U.S. PATENT DOCUMENTS

| 6,503,272 | B2 | 1/2003 | Duerig et al. |
| 6,969,367 | B2 | 11/2005 | Tu et al. |
| 7,201,772 | B2 | 4/2007 | Schwammenthal et al. |
| 7,226,429 | B2 | 6/2007 | Tullis |
| 7,314,460 | B2 | 1/2008 | Tu et al. |
| 2002/0017503 | A1 | 2/2002 | Banas et al. |
| 2004/0243219 | A1 | 12/2004 | Fischer et al. |
| 2006/0064174 | A1 | 3/2006 | Zadno |
| 2006/0161250 | A1 | 7/2006 | Shaw |
| 2006/0167543 | A1 | 7/2006 | Bailey et al. |
| 2007/0055365 | A1 | 3/2007 | Greenberg et al. |
| 2007/0129791 | A1 | 6/2007 | Balaji |
| 2009/0117168 | A1 | 5/2009 | Keenan |

FOREIGN PATENT DOCUMENTS

| CN | 1531978 A | 9/2004 |
| CN | 1814310 A | 8/2006 |
| JP | 8191876 A | 7/1996 |
| WO | 03105990 A2 | 12/2003 |
| WO | 2009023332 A2 | 2/2009 |

OTHER PUBLICATIONS

International Search Report in corresponding Application No. PCT/US11/57669, mailed Mar. 14, 2012, 2 pgs.

Primary Examiner — John Kim
(74) Attorney, Agent, or Firm — Wood, Herron & Evans, LLP

(57) ABSTRACT

An anti-viral device including a body having at least one side wall defining an interior space therein. The body has opposite first and second open ends, the open ends also defined by the at least one side wall and in fluid communication with the interior space. The device further includes at least one flap operatively connected to the at least one side wall and extending into the interior space from the at least one sidewall toward the longitudinal axis of the body, the at least one flap being flexible. And, the device also includes at least one groove disposed in a surface of the at least one flap.

18 Claims, 5 Drawing Sheets

ANTI-VIRAL DEVICE

FIELD OF INVENTION

The present invention is directed generally to medical devices, and more specifically to a device that reduces or eliminates viral load in a subject.

BACKGROUND

This section is intended to introduce the reader to various aspects of art that may be related to various aspects of the present invention, which are described and/or claimed below. This discussion is believed to be helpful in providing the reader with background information to facilitate a better understanding of various aspects of the present invention. Accordingly, it should be understood that these statements are to be read in this light, and not as admissions of prior art.

As is known to those of ordinary skill in the art, a virus is an infectious agent that replicates inside the living cells of organisms. Viruses infect all types of organisms, including bacteria, plants, and animals. Examples of common human diseases caused by viruses include the common cold, influenza, chickenpox, and cold sores. Many serious diseases such as Ebola, AIDS, avian influenza, and SARS are caused by viruses. Since the initial discovery of tobacco mosaic virus in the late 1800s, thousands of viruses have been identified. Viruses are ubiquitous and are one of the most abundant biological entities.

Viruses include at least two components: (1) genetic material (either DNA or RNA); and (2) a protein coat (the capsid) that surrounds and protects the genetic material. Additionally, in some cases (e.g., in many animal viruses), an envelope of lipids surrounds the protein coat.

Viruses generally enter a host cell in one of two ways. First, the capsid or viral envelope can fuse with the host cell membrane and release the viral material into the host cell. Second, the virus may attach to surface molecules of the host cell, (usually receptors that bind molecules essential to cell's function), and are then passively carried into the cell. In either method, the virus is able to penetrate the cell's membrane and enter the cell. Once inside the cell, the host cell generally breaks down the capsid and viral envelope, thereby exposing the genetic material of the virus. The viral nucleic acid (whether DNA or RNA) then takes over the host cell, using the host cell's own machinery to replicate itself. The virus replicates its genetic material and initiates synthesis of capsid proteins, which spontaneously self-assemble to form the capsid. Non-enveloped viruses are usually then released from the host cell by lysis (the virus causes the lysis of the cell, or the body's own immune system causes lysis). Enveloped viruses are usually released by budding from the host cell and using part of the host cell membrane as their viral envelopes.

As described above, viral mechanisms at the cellular level include cell lysis: the breaking open and subsequent death of the cell. In multicellular organisms, if enough cells die, the whole organism will start to suffer the effects. Although viruses cause disruption of healthy homeostasis, resulting in disease, they may exist relatively harmlessly within an organism. An example would include the ability of the herpes simplex virus, which causes cold sores, to remain in a dormant state within the human body. This is a characteristic of the herpes viruses including Epstein-Barr virus, which causes glandular fever, and varicella zoster virus, which causes chickenpox. Some viruses can cause life-long or chronic infections, where the viruses continue to replicate in the body despite the host's defense mechanisms (common in hepatitis B and hepatitis C virus infections). People chronically infected are known as carriers, as they serve as reservoirs of infectious virus.

Most viral infections of humans and other animals have incubation periods during which the infection causes no signs or symptoms. Incubation periods for viral diseases generally range from a few days to weeks. Somewhat overlapping, but mainly following the incubation period, there is a period of communicability; a time when an infected individual or animal is contagious and can infect another person or animal. This too is known for many viral infections and knowledge the length of both periods is important in the control of outbreaks.

Viruses can be transmitted in many ways. Influenza viruses are spread by coughing and sneezing. The norovirus and rotavirus, common causes of viral gastroenteritis, are transmitted by the fecal-oral route and are passed from person to person by contact, entering the body in food or water. HIV is one of several viruses transmitted through sexual contact and by exposure to infected blood. Transmission of viruses can be vertical (e.g., from mother to child) or horizontal (e.g., from person to person). Examples of vertical transmission include hepatitis B virus and HIV where a baby is born already infected with the virus. Horizontal transmission is the most common mechanism of spread of viruses in populations. Transmission can be exchange of blood by sexual activity, by mouth by exchange of saliva, or from contaminated food or water, by breathing in viruses in the form of aerosols, and by insect vectors such as mosquitoes.

There are many methods for combating viruses. Viral infections in animals provoke an immune response that usually eliminates the infecting virus. Immune responses can also be produced by vaccines, which confer an artificially acquired immunity to the specific viral infection. However, some viruses (including those causing AIDS and viral hepatitis) evade these immune responses and result in chronic infections. Antibiotics have no effect on viruses, but several antiviral drugs have been developed.

Thus, one line of defense against viruses is the body's immune system, which includes the innate immune system and the adaptive immune system. The innate immune system comprises cells and other mechanisms that defend the host from infection in a non-specific manner. This means that the cells of the innate immune system recognize and respond to pathogens in a generic way, but unlike the adaptive immune system, it does not confer long-lasting or protective immunity to the host.

When the adaptive immune system of a vertebrate encounters a virus, it produces specific antibodies that bind to the virus and render it non-infectious. This is called humoral immunity. Two types of antibodies are important: IgM and IgG. IgM is highly effective at neutralizing viruses but is only produced by the cells of the immune system for a few weeks. IgG is produced indefinitely.

A second defense of vertebrates against viruses is cell-mediated immunity and involves immune cells known as T cells. The body's cells constantly display short fragments of their proteins on the cell's surface, and if a T cell recognizes a suspicious viral fragment there, the host cell is destroyed by killer T cells and the virus-specific T-cells proliferate.

However, as described above, not all virus infections produce a protective immune response. For example, these persistent viruses evade immune control by sequestration, blockade of antigen presentation, cytokine resistance, evasion of natural killer cell activities, escape from apoptosis, and antigenic shift. Other viruses, called neurotropic viruses, are disseminated by neural spread where the immune system may be unable to reach them. And, HIV evades the immune system by constantly changing the amino acid sequence of the proteins on the surface of the virion.

Vaccination is a cheap and effective way of preventing infections by viruses. Vaccines were used to prevent viral infections long before the discovery of the actual viruses. Vaccines can consist of live-attenuated or killed viruses, or viral proteins (antigens). Live vaccines contain weakened forms of the virus, which do not cause the disease but nonetheless confer immunity. Live vaccines can be dangerous when given to people with a weak immunity, because in these people the weakened virus can cause the original disease. Biotechnology and genetic engineering techniques are used to produce subunit vaccines. These vaccines use only the capsid proteins of the virus. Hepatitis B vaccine is an example of this type of vaccine.

Unfortunately, vaccinations may not be useful once a person has already been infected. And it is not realistically possible to immunize individuals against all viruses, due to the sheer number of viruses, the costs that would entail, any risks of contraction of disease, and the fact that there are some viruses for which there is no vaccine.

And so, anti-viral drugs may be used to treat viral infection. Antiviral drugs are often nucleoside analogues, (simulated DNA building blocks), which viruses mistakenly incorporate into their genomes during replication. The life-cycle of the virus is then halted because the newly synthesized DNA is inactive. This is because these analogues lack the hydroxyl groups, which, along with phosphorus atoms, link together to form the strong "backbone" of the DNA molecule. Examples of nucleoside analogues are aciclovir for Herpes simplex virus infections and lamivudine for HIV and Hepatitis B virus infections. Other antiviral drugs in use target different stages of the viral life cycle. HIV is dependent on a proteolytic enzyme called the HIV-1 protease for it to become fully infectious. There is a large class of drugs called protease inhibitors that inactivate this enzyme.

However, because viruses use vital metabolic pathways within host cells to replicate, they are difficult to eliminate without using drugs that cause toxic effects to host cells in general. And so, unfortunately, there are drawbacks associated with all the above methods for combating viral infection.

SUMMARY

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

The various aspects of the present invention are related to a device that reduces or eliminates viral load in a subject. As is known to those of ordinary skill in the art, "viral load" is a measure of the severity of a viral infection, and can be calculated by estimating the amount of virus in an involved body fluid. The device, in one aspect, provides a physical structure to mechanically reduce viral load (and which may be implanted in a subject). As a result, it does not suffer from the drawbacks listed above for other methods of combating viruses (e.g., vaccines and anti-viral drugs). Embodiments of the device include a body having at least one side wall defining an interior space therein. The body also defines opposite first and second open ends, (i.e., defined by the at least one side wall), the open first and second ends being in fluid communication with the interior space and in fluid communication with one another (e.g., via the interior space). At least one flap is operatively connected to the at least one side wall and extends into the interior space from the at least one sidewall. The at least one flap may be flexible. Further, the at least one flap includes at least one groove disposed in a surface thereof.

The device is used such that blood is caused to flow through the interior space of the body, from one of the first and second ends to the other of the first and second ends. The blood may be from a subject infected with a virus, such that the blood includes cells infected with viruses. As was described above, during infection, the virus initially confronts and/or attaches to the outer surface of the host cell. Thus, the virus is present on the outer surface of the cell at that time. As blood passes through the body of the device, the at least one flap contacts and rubs the outer surface of a blood cell. As this occurs, the at least one flap bends back in the direction of the blood flow. And, as this occurs, the size of the at least one groove on the surface of the at least one flap increases (due to the malleable material of the flap or flaps). The groove or grooves are cut at an angle, such that they scoop virus on the surface of the cell, trapping the virus in the groove as the blood cell passes through the interior space.

Once the cell is no longer in contact with the flap, the flap returns to its normal position, and the width of the grooves return to their non-expanded size, thereby crushing the virus in the groove. In order to crush the virus (and render it inert), the width of the groove may be cut smaller than the width of the virus one desires to reduce/eliminate. For example, if the virus has a width of 120 nm, grooves could be cut with a nonexpanded width less than 120 nm (for example, at 80 nm to 90 nm) to insure that the virus is crushed, so genetic material escapes the capsid and is rendered inert. While the groove is cut at a non-expanded width that is smaller than the width of the virus to be reduced/eliminated, the width of the groove is also such that it can expand to at least the width of the virus (in the example above, 120 nm), or more. Each flap may also include multiple grooves, including grooves of different widths.

In one embodiment, the device may be implanted in a blood vessel of a subject. Thus, the body of the device may be a stent (or similar to a stent). As is well known, stents are normally used to increase the diameter of a blood vessel for greater blood flow and/or to support or stabilize a blood vessel. Such stents are generally tubular in their shape (although such shape is not essential to the present invention), and blood flow passes through an interior space defined by the side wall of the body. In an anti-viral stent, blood cells would be funneled through this interior space.

While the anti-viral device could be implanted in the blood vessel of a subject, another option would be use of the anti-viral device in an apparatus to reduce and/or eliminate viral load in blood. In such an option, an anti-viral apparatus may include a housing having a conduit present therein for the passage of fluids. The conduit includes an interior space through which fluid passes. The apparatus also includes at least one flap extending into the interior space. As above, the at least one flap may be flexible, and include at least one groove disposed in a surface thereof. The apparatus could be optimized to pump the blood through the interior space as efficiently as possible. For example, the machine could be engineered to open and close the flap or flaps so only one blood cell would pass through at a time, increasing the odds of scooping viruses per blood cell.

BRIEF DESCRIPTION OF DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

DETAILED DESCRIPTION

Figure 1:
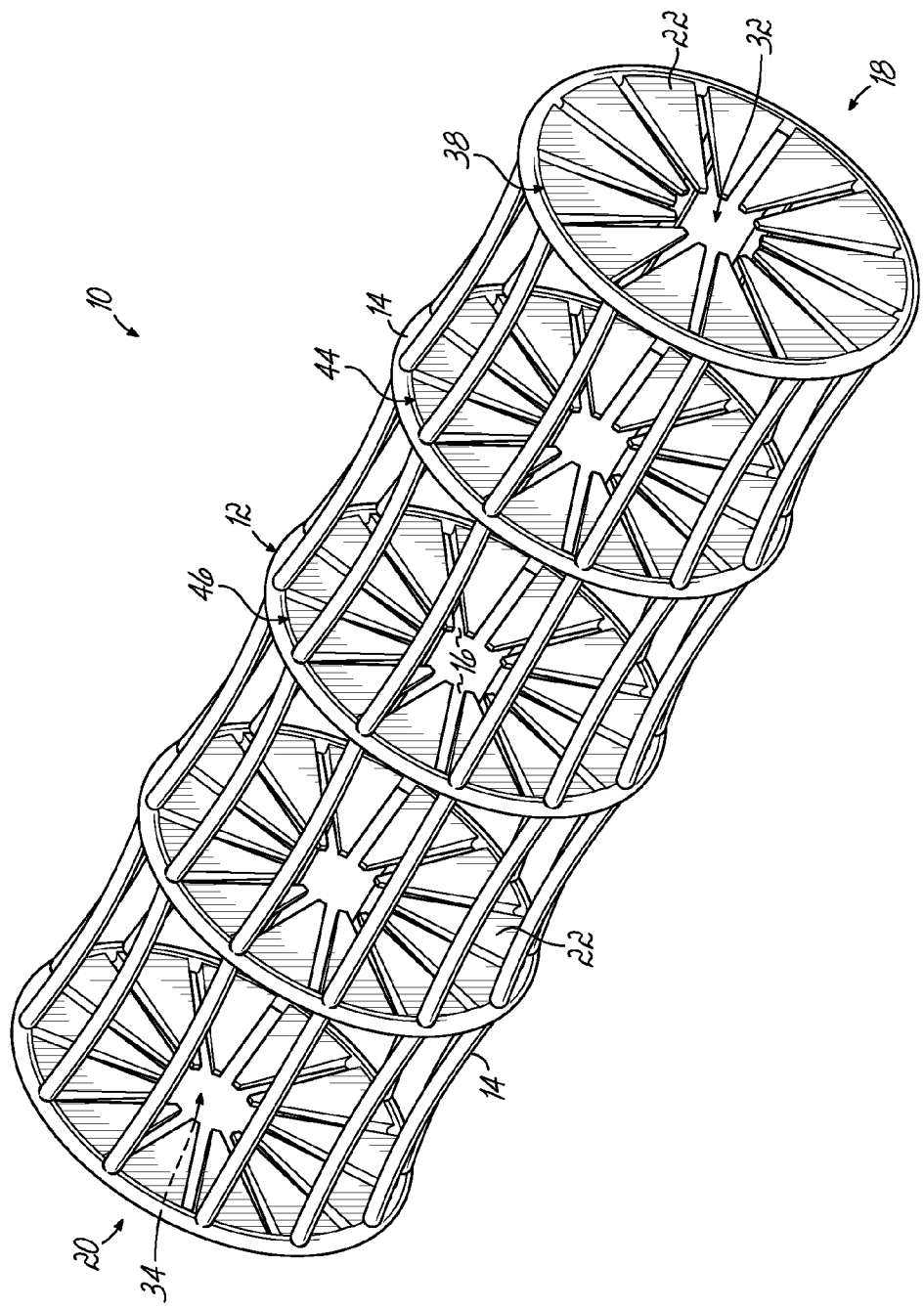
FIG. 1 is a perspective view of one exemplary embodiment of the device of the present invention.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The various aspects of the present invention are related to a device that reduces or eliminates viral load in a subject. As is known to those of ordinary skill in the art, "viral load" is a measure of the severity of a viral infection, and can be calculated by estimating the amount of virus in an involved body fluid. The device, in one aspect, provides a physical structure to mechanically reduce viral load (and which may be implanted in a subject). As a result, it does not suffer from the drawbacks listed above for other methods of combating viruses (e.g., vaccines and anti-viral drugs).

Referring now to the Figures, embodiments of the device 10 include a body 12 having at least one side wall 14 defining an interior space 16 therein. The body 12 also defines opposite first and second open ends 18, 20, (e.g., defined by the at least one side wall 14), the open first and second ends 18, 20 in fluid communication with the interior space 16 and in fluid communication with one another via the interior space 16. At least one flap 22 is operatively connected to the at least one side wall 14 and extends into the interior space 16 from the at least one sidewall 14. The at least one flap 22 may be flexible. Further, the at least one flap 22 includes at least one groove 24 disposed in a surface thereof.

The device 10 is used such that blood is caused to flow through the interior space 16 of the body 12, from one of the first and second ends 18, 20 to the other of the first and second ends 18, 20. The blood may be from a subject infected with a virus, such that the blood includes cells 26 infected with viruses 30. As was described above, during infection, the virus 30 initially confronts and/or attaches to the outer surface of the host cell. Thus, the virus 30 is present on the outer surface of the cell 26 at that time. As blood passes through the body 12 of the device, the at least one flap 22 contacts and rubs an outer surface of a blood cell 26. As this occurs, the at least one flap 22 bends back in the direction of the blood flow 28. As this occurs, the size of the at least one groove 24 on the surface of the at least one flap 22 increases (due to the flexible and malleable material of the flap 22 or flaps). The groove 24 or grooves are cut at an angle, such that they scoop virus 30 on the surface of the cell, trapping the virus 30 in the groove 24 as the blood cell 26 passes through the interior space 16. For example, as in the illustrated embodiment, a surface of the groove (such as a bottom surface) may be disposed at an upward slope in a direction from the side of the flap absent of grooves to the side of the flap including grooves (an "upward" slope when the flap is oriented with the portion of the flap associated with the body being the top of the flap, and the free end of the flap being the bottom of the flap). Those of ordinary skill in the art will recognize that in alternate embodiments, grooves may be disposed on both sides of the flap.

Once the cell 26 is no longer in contact with the flap 22, the flap 22 returns to its normal position, and the width of the groove 24 returns to its non-expanded size, thereby crushing the virus 30 in the groove 24. In order to crush the virus 30 (and render it inert), the width of the groove 24 will be cut smaller than the width of the virus 30 one desires to reduce/eliminate. For example, if the virus 30 has a width of 120 nm, grooves could be cut with a nonexpanded width less than 120 nm (for example, at 80 nm to 90 nm) to insure that the virus 30 is crushed, so genetic material escapes the capsid and is rendered inert. While the groove 24 is cut at a non-expanded width that is smaller than the width of the virus 30 to be reduced/eliminated, the width of the groove 24 is also such that it can expand to at least the width of the virus 30 (in the example above, 120 nm), or more. Each flap 22 may also include multiple grooves, including grooves of different widths. It is within the knowledge of one of ordinary skill in the art to determine sizes of viruses and size the groove or grooves accordingly.

More specifically, FIG. 1 shows a perspective view of one exemplary embodiment of an anti-viral device 10 in accordance with the principles of the present invention. The device 10 includes first and second openings 32, 34 at opposite first and second ends 18, 20, respectively, of the device 10. The body 12, in the illustrated embodiment, has a generally cylindrical shape, whereby the side wall 14 extends between the first end 18 and the second end 20. Thus, in the illustrated embodiment, the side wall 14 defines the interior space 16.

Those of ordinary skill in the art will recognize that the at least one sidewall 14 does not have to be a solid wall, but can have other structures, such as an open framework (as shown in the illustrated, exemplary embodiment of FIG. 1). Thus, those of ordinary skill in the art will appreciate that any structure (an open structure, such as struts, meshwork, etc.; a closed structure, such as a solid wall; or a combination of the two) can be used as the at least one side wall 14. Further, while the body 12 of the device 10 in the illustrated embodiment is generally cylindrical (having a substantially circular cross-section at the side wall 14), those of ordinary skill in the art will recognize that the shape of the body 12 is not limiting, and further shapes (square, hexagonal, trapezoidal, oval, etc. cross-sections) are possible. Additionally then, those of ordinary skill in the art will recognize that multiple side walls may be used to form the body. And so a body 12 having "at least one side wall," as used herein, allows for bodies with one side wall 14 or more than one side wall.

Further, those skilled in the art will recognize that there are various materials that can be used in preparing the device 10. In general, the materials used for the device 10 (e.g., the at least one side wall) may be flexible, supportive, capable of expansion, and/or biocompatible. There are several materials that may be used in such construction, and which are typically used in the construction of devices such as stents. For example, most stents are built on a stainless steel platform. However, stainless steel may not be fully compatible with the human body. As such, alternative materials such as gold, titanium, cobalt-chromium alloy, tantalum alloy, nitinol and several types of polymer (e.g., silicone, polyethylene, polyurethane, etc.) may be used. This list is not limiting. Materials that are not biocompatible can cause a number of complications. And so, the device 10 may be prepared with a material or materials to not cause a reaction in the body of the subject.

Further, some polymers are biodegradable, bioabsorbable, or bioerodible and may be used. For example, biodegradable or bioabsorbable stents contain a component (such as an enzyme or microbe) that degrades quickly enough to make them appropriate for short-term uses (which may be useful in applications where the device 10 can clear a virus 30 from the subject, and then degrade of its own accord). Biodegradable materials can also form an effective coating for the device because they can be mixed with an antirestinotic drug and will degrade within a few weeks, thus releasing the drug into the surrounding tissue and reducing the risk of restenosis. Non-limiting examples of biodegradable polymers are: polyesters, polyorthoesters and polyanhydrides. Collagen is also very biocompatible and reduces the rate of restenosis and thrombosis. In addition, anticoagulants and fibrinolytic agents bound to the collagen can aid in drug delivery. Those of ordinary skill in the art will be able to determine materials that can be used in such implants (for the structure, for coatings, or for both) and the particular material is not limiting.

In one embodiment, the device 10 may be implanted in a blood vessel of a subject. Thus, the device 10 may be a stent, similar to a stent, or incorporate a stent. As is well known, stents are normally used to increase the diameter of a blood vessel for greater blood flow and/or to support or stabilize a blood vessel. Such stents are generally tubular in their shape, and blood flow 28 passes through an interior space 16 defined by the side wall 14 of the body 12. In the anti-viral stent, blood cells 26 would be funneled through this interior space. Stents have been developed for use in various lumens of the body, including the biliary tree, venous system, peripheral arteries, and coronary arteries. Stents are generally used to open or hold open a lumen that has been blocked (occluded) or reduced in size (stenosed) by some disease process (e.g., atherosclerosis, cancer, etc.). Previously developed stents for use in the biliary, venous, and arterial systems have been of two broad classes: balloon-expanded and self-expanding.

Stents generally possess a number of definite properties. First, stents generally provide unobstructed motion of body fluids through the implanted structure without deteriorating metabolic processes in tissues (when used in the present invention, those of ordinary skill in the art will recognize that "unobstructed" motion includes motion through a conduit including flaps). Second, stents generally are rigid enough to withstand the pressure exerted by the walls of blood vessels and body cavities, to provide uniform pressure distribution over the surface being prosthesized, and the same time possesses elasticity. Third, the stent construction is generally convenient for being transported to the zone of reconstruction and positioned there, as well not produce any injurious effect upon the surrounding tissues in the course of implantation and further functioning.

In addition to the features described above, the device 10 (whether a stent or other device) may be coated with a compound or compounds that reduce or prevent immune response in the subject. Further, the device 10 (whether a stent or other device) may be coated with a compound or compounds that promote cell growth on a surface of the device. This may be helpful, for example, in promoting a symbiosis between the device 10 and any blood vessel in which it is implanted.

Figure 2:
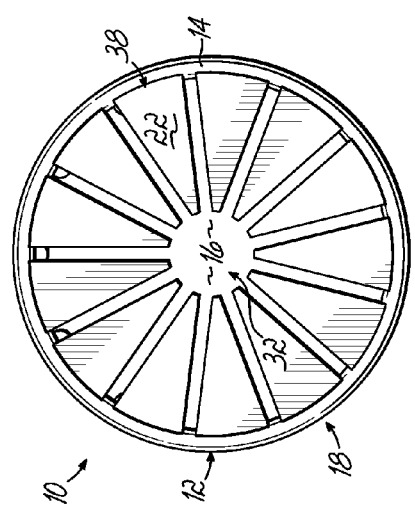
FIG. 2 is an end view of the exemplary embodiment of FIG. 1.
Figure 3:
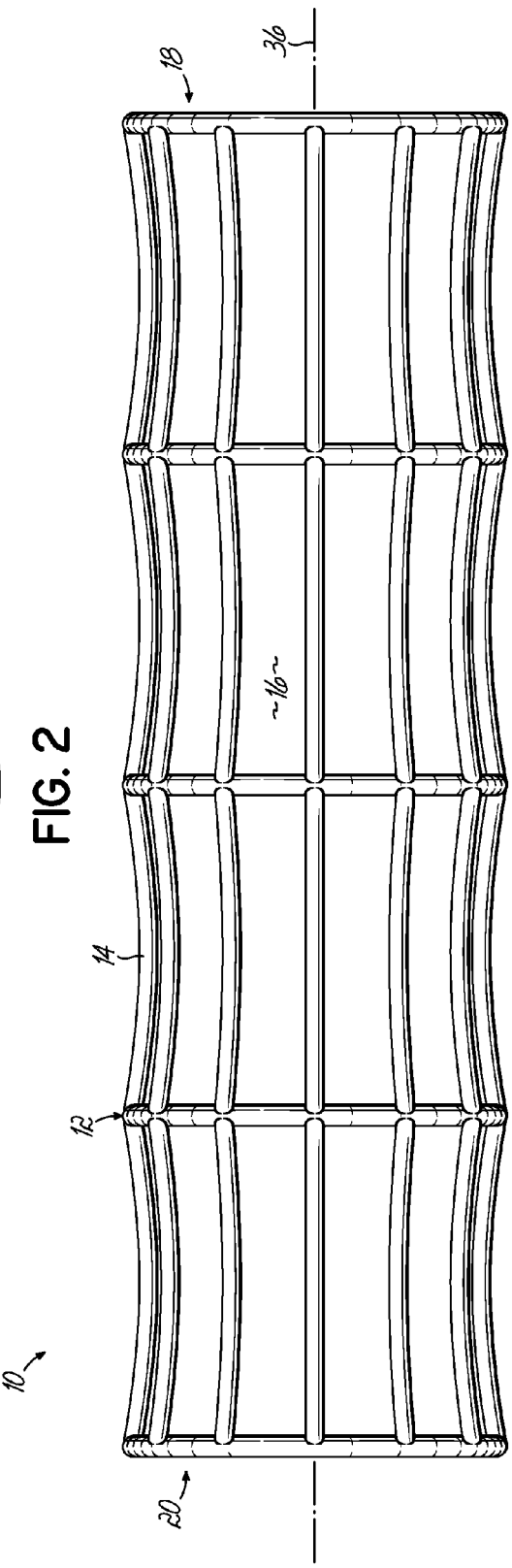
FIG. 3 is a side view of the exemplary embodiment of FIG. 1.
Figure 4:
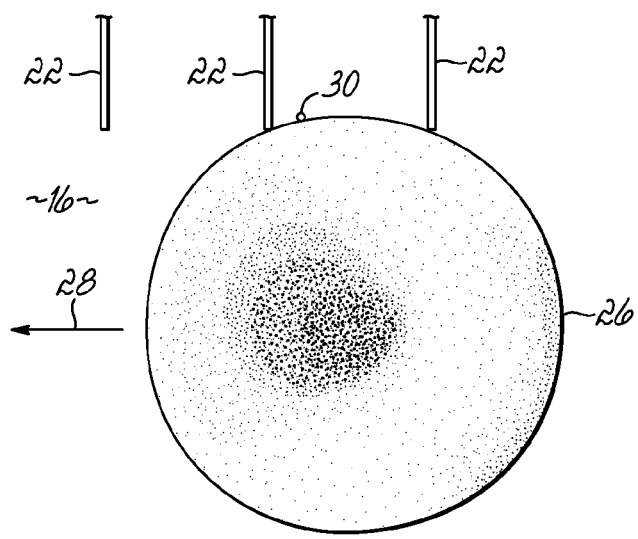
FIG. 4 is a schematic representation of the end portion of flaps of the device of an embodiment of the present invention interacting with a virus-infected cell.

As described above, and referring to FIGS. 1-3, the device 10 also includes at least one flap 22. In general, the at least one flap 22 is associated with (such as by being operatively connected to) the at least one side wall 14 of the device, and extends into the interior space 16 from the at least one sidewall 14 (such as toward a longitudinal axis 36 of the body 12), the at least one flap 22 being flexible. The term "at least one flap" means that the device 10 may include one flap 22 or may include more than one flap. Thus, in one exemplary embodiment of the device, as illustrated in FIGS. 1-3, the at least one flap 22 may be a member of a plurality of flaps 38. As can be seen from the illustrated embodiment, each flap 22 of the plurality of flaps 38 extends into the interior space 16 of the device 10 from the at least one sidewall 14 (e.g., generally toward the longitudinal axis 36 of the body 12). Further, as can be seen from the illustrated embodiment and as described above, the plurality of flaps 38 may be molded as a part of the side wall 14 of the body. However, as will be recognized by those of ordinary skill in the art, the flaps do not need to be molded monolithically with the side wall 14 of the body, but rather may be a separate component that is affixed to the interior surface of the side wall 14 of the body 12. Further, in the illustrated embodiment, each flap 22 of the plurality of flaps 38 is flexible. In order to achieve flexibility, the at least one flap 22 may include similar materials to those described above with respect to the body 12 of the device 10 itself in its construction. However, the particular material used for the flap 22 or flaps of the device 10 is not limiting. Further, as can be seen from the Figures, the at least one flap 22 is triangular in shape in the illustrated embodiment. However, those of ordinary skill in the art will recognize that such a shape is merely exemplary, and other shapes may be used.

As the at least one flap 22 is flexible, it is adapted to move between a first position 40 and a second position 42. In general, in the exemplary illustrated embodiment, the first position 40 is substantially perpendicular to the longitudinal axis 36 of the body 12 (see FIGS. 1-3) and the second position 42 is substantially other than perpendicular to the longitudinal axis 36 of the body 12 (see FIG. 6). The at least one flap 22 may be adapted to move between the first and second positions 40, 42 in response to contact by a blood component, for example a blood cell 26. The particular degree of rigidity or flexibility of the flap or flaps may generally be that which suffices to reduce viral load within a subject, and determining this is within the knowledge of one of ordinary skill in the art. (Further, not all flaps need the same degree of flexibility).

Further, as can be seen from the Figures, the device 10 may include multiple sets of flaps. Thus, in certain embodiments, such as the illustrated embodiment, the plurality of flaps 38 includes multiple subsets of flaps, each subset of flaps including at least one flap 22. Thus, at a minimum, the multiple subsets of flaps includes at least a first subset 44 and a second subset 46 spaced apart from one another along the body 12 of the device 10.

In one embodiment, each flap 22 of the plurality of flaps 38 may be generally coplanar with each of the other flaps 22 of the plurality of flaps 38 (when in the first position). Thus, the flaps 22 of the plurality of flaps 38 may be spaced equidistant from one another and in the same plane around the circumference of the cylindrical side wall 14 of the illustrated embodiment. However, as will be apparent to those of ordinary skill in the art, it is not necessary that the flaps 22 that lie in the same plane be equidistant from one another about the interior surface of the side wall 14.

Additionally or alternatively, and referring particularly to FIG. 1, the plurality of flaps 38 may include at least a first subset 44 of flaps and a second subset 46 of flaps. In such an embodiment, each flap 22 of the first subset 44 of flaps is generally coplanar with each of the other flaps of the first subset 44 of flaps (when in the first position) along a first plane, and each flap 22 of the second subset 46 of flaps is generally coplanar with each of the other flaps of the second subset 46 of flaps (when in the first position) along a second plane, with the second plane not being coplanar with the first plane. There may be additional (i.e., third, fourth, fifth) subsets of flaps that each lie in their own planes, which are separate from the first and second planes. Further, as can be seen in the illustrated embodiment (see FIG. 2), there are thirteen such flaps located in one plane around the circumference of the side wall. However, as will be apparent to those of ordinary skill in the art, thirteen is not a required number of flaps to the invention, and there is no particular number of flaps which is necessary to the invention of the present application. Further, while a plurality of flaps is shown, it will be recognized by those skilled in the art that a flap 22 may be a continuous ring about the interior compartment.

Returning to FIGS. 1-3, the flaps are preferably biased toward the first position. When the fluid flow pressure exceeds a certain level to overcome the torsional force and/or when the flap or flaps are contacted by an object in the fluid (e.g., blood cell 26), the flaps 22 move to the second position 42. Or, the flaps can be biased such that fluid flow is not sufficient to move the flaps 22 substantially from the first position 40, but rather a component of blood (e.g., a cell) is necessary to substantially move the flaps.

Further, as described above, the device 10 includes at least one groove 24 disposed in a surface of the at least one flap. The groove 24 or grooves can be seen at least in FIGS. 5-7. "At least one groove" means that the flap 22 may include one groove 24 or more than one groove. Further, in embodiments including a plurality of flaps 38 and/or multiple subsets of pluralities of flaps, the flaps may include one groove 24 on each flap 22, more than one groove 24 on each flap 22, or differing numbers of grooves on each flap 22 (as compared to the number of grooves on other flaps). Further, certain flaps 22 of the plurality of flaps 38 may have no grooves at all. The grooves are cut at an angle, such that they scoop any virus 30 on the surface of the cell, trapping the virus 30 in the groove 24 as the blood cell 26 passes through. When the flap 22 returns to its normal position, the gap in the grooves would no longer be at an expanded size, crushing the virus 30 in the groove. Thus, the size of the groove 24 will be cut smaller than the virus 30 one desires to treat.

As described above, the grooves 24 are cut at an angle, such that they scoop any virus 30 on the surface of the cell, trapping the virus 30 in the groove 24 as the blood cell 26 passes through the body 12. As can be seen in the cross section of the flap 22 of FIG. 5, the groove 24 is depicted as having a top surface, bottom surface, and connecting surface (connecting the top and bottom surfaces). As can be seen in that embodiment, both the top surface and bottom surface of the groove are angled with respect to a longitudinal axis of the flap 22 and, in the illustrated embodiment, the top surface and bottom surface are at different angles to one another compared to the longitudinal axis of the flap. It will be recognized by those of ordinary skill in the art that the particular angles, and configuration of angles, depicted in FIGS. 5, 6, and 7 are merely exemplary.

Figure 5:
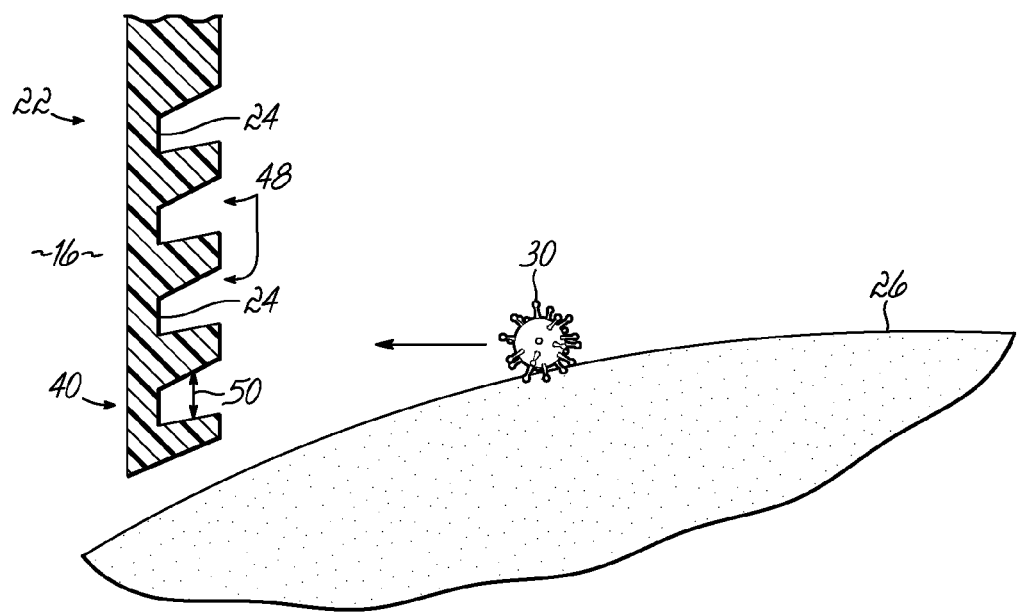
FIG. 5 is an enlarged view of an end portion of a flap of a device of an embodiment of the present invention prior to contact with a virus and virus-infected cell.
Figure 6:
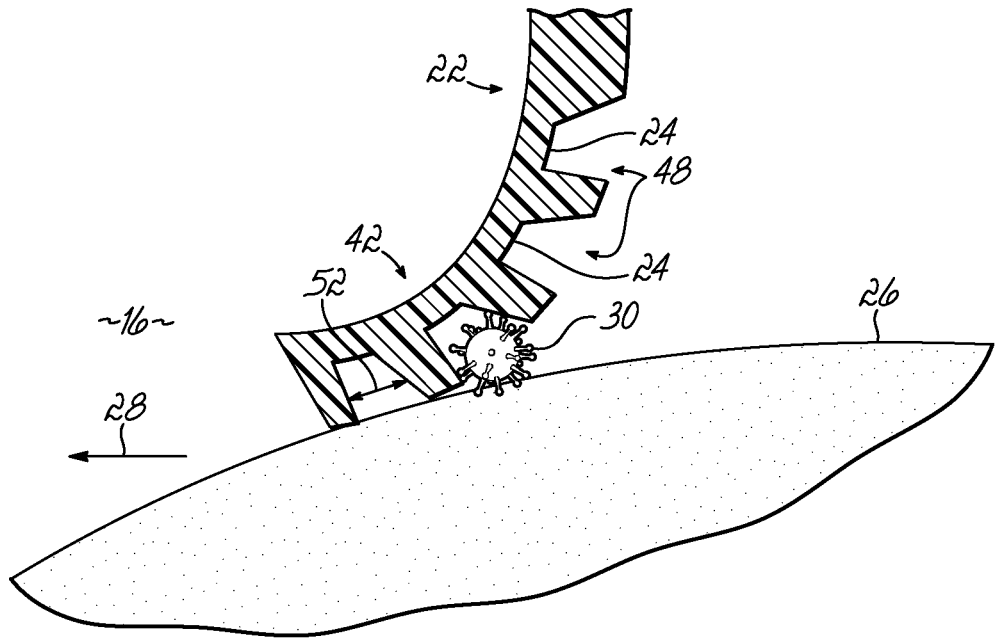
FIG. 6 is an enlarged view of an end portion of a flap of a device of an embodiment of the present invention in contact with a virus and virus-infected cell.
Figure 7:
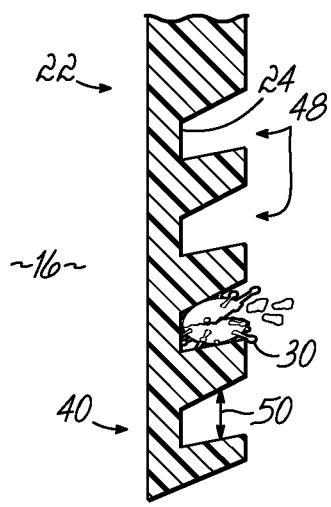
FIG. 7 is an enlarged view of an end portion of a flap of a device of an embodiment of the present invention in contact with a virus and no longer in contact with a cell.

In the illustrated embodiment of FIGS. 5-7, the at least one groove 24 is a member of a plurality of grooves, each groove 24 of the plurality of grooves 48 being disposed in a surface of a flap 22 of the plurality of flaps.

Further, the at least one groove 24 moves between a non-expanded condition 50 and an expanded condition 52 as the at least one flap 22 moves between first and second positions 40, 42 (due to the flexible and malleable nature of the at least one flap). Thus, in one exemplary embodiment, the at least one groove 24 is in the non-expanded condition 50 when the at least one flap 22 is in the first position 40 (See FIG. 5), and the at least one groove 24 is in the expanded condition 52 when the at least one flap 22 is in the second position 42 (See FIG. 6). As such, the at least one groove 24 is sized at least as large as, and often larger than, a virus 30 the device 10 is adapted to reduce, when the at least one groove 24 is in the expanded condition 52. And, the at least one groove 24 is sized smaller than a virus 30 the device 10 is adapted to reduce, when the at least one groove 24 is in the non-expanded condition 50.

Referring now to FIGS. 4-7, the device 10 is used such that blood is caused to flow through the interior space 16 of the body, from one of the first and second ends 18, 20 to the other of the first and second ends 18, 20. The blood may be from a subject infected with a virus, such that the blood includes cells 26 infected with viruses 30. As blood passes through the body 12, the at least one flap 22 contacts and rubs the outer surface of a blood cell 26, which bends the at least one flap 22 back the direction of the blood flow. As this occurs, the size of the at least groove 24 on the surface of the at least one flap 22 increases (due to the malleable material of the flap 22 or flaps) the groove 24 or grooves are cut at an angle, such that they scoop any virus 30 on the surface of the cell, trapping the virus 30 in the groove 24 as the blood cell 26 passes through the interior space.

Once the cell 26 is no longer in contact with the flap, the flap 22 returns to its normal position, and the width of the grooves return to their non-expanded size, thereby crushing the virus 30 in the groove. In order to crush the virus 30 (and render it inert), the width of the groove 24 may be cut smaller than the width of the virus 30 one desires to reduce/eliminate. For example, if the virus 30 has a width of 120 nm, grooves could be cut with a nonexpanded width less than 120 nm (for example, at 80 nm to 90 nm) to insure that the virus 30 is crushed, so genetic material escapes the capsid and is rendered inert. While the groove 24 is cut at a non-expanded width that is smaller than the width of the virus 30 to be reduced/eliminated, the width of the groove 24 is also such that it can expand to at least the width of the virus 30 (in the example above, 120 nm), or more. Each flap 22 may also include multiple grooves, including grooves of different widths.

Figure 8:
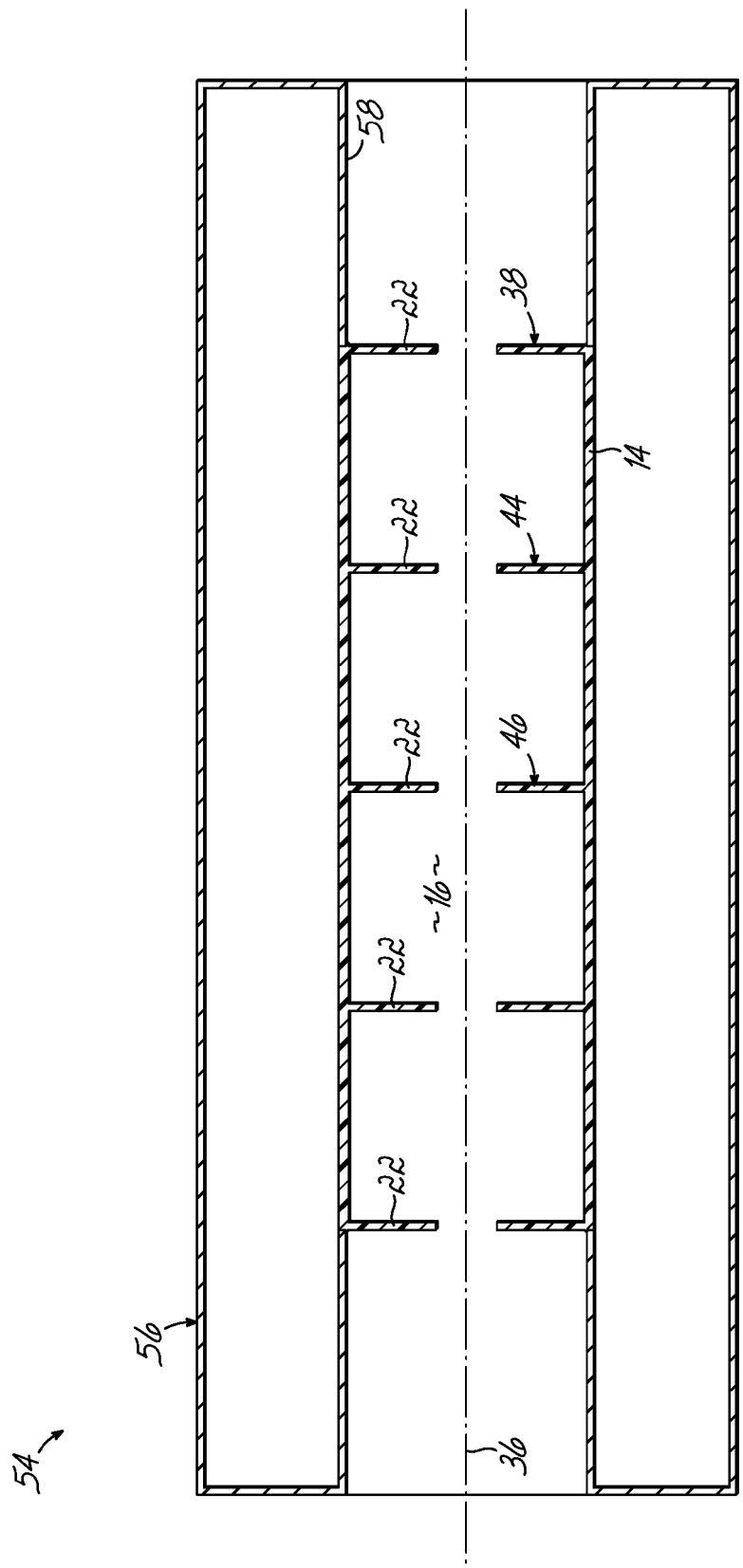
FIG. 8 is a schematic cutaway view of an exemplary apparatus including a conduit according to the principles of the present invention.

While the anti-viral stent could be implanted in the blood vessel of a subject, another option would be use of the anti-viral device 10 in an apparatus, or the principles of the device 10 in an apparatus, to reduce and/or eliminate viral load in a subject. In such an option, and referring now to FIG. 8, an anti-viral apparatus 54 may include a housing 56 having a conduit 58 for the passage of fluids. The conduit 58 includes an interior space 16 through which fluid passes. The apparatus 54 also includes at least one flap 22 operatively connected to the conduit 58 and extending into the interior space. As above, the at least one flap 22 may be flexible, and include at least one groove 24 (as in FIGS. 5-7) disposed in a surface thereof. The apparatus 54 could be optimized to pump the blood through the interior space 16 as efficiently as possible. For example, the machine could be engineered to open and close the flap 22 or flaps so only one blood cell 26 would pass through at a time, increasing the odds of scooping viruses per blood cell.

The subject's blood is then pumped through the conduit of the apparatus, exposing it to the at least one flap 22 and at least one groove 24. Blood flows through the conduit, which operates as described above with respect to the device. The treated blood is then returned via a circuit back to the subject's body. Treatments may be given in multiple ways. For example treatments may be given in a treatment center at various times. Alternatively, people may be treated at home more frequently for various treatment lengths (as home treatment is a flexible modality and schedules can be changed day to day, week to week).

The apparatus 54 may function in a manner similar to that of the device 10 that is implanted into a subject. And so, the principles of the device, as they would work in the apparatus, will be briefly discussed with respect to FIGS. 1-7. In general, the at least one flap 22 is operatively connected to the at least one side wall 14 of the conduit, and extends into the interior space 16 from the at least one sidewall 14, the at least one flap 22 being flexible. The at least one flap 22 may be a member of a plurality of flaps. As can be seen from the illustrated embodiment, each flap 22 of the plurality of flaps 38 extends into the interior space 16 of the conduit from the at least one sidewall 14 generally toward the longitudinal axis 36 of the conduit. Further, as can be seen from the illustrated embodiment and as described above, the plurality of flaps 38 may be molded as a part of the side wall 14 of the conduit. However, as will be recognized by those of ordinary skill in the art, the flaps do not need to be molded monolithically with the side wall 14 of the conduit, but rather may be a separate component that is affixed to the interior surface of the side wall 14 of the conduit. Further, in the illustrated embodiment, each flap 22 of the plurality of flaps 38 is flexible. In order to achieve flexibility, the at least one flap 22 may include similar materials to those described above with respect to the body 12 of the device 10 itself in its construction. However, the particular material used for the flap 22 or flaps of the apparatus 54 is not limiting.

As the at least one flap 22 is flexible, it is adapted to move between first and second positions. In general, the first position 40 is substantially perpendicular to the longitudinal axis 36 (same as in the embodiment shown in FIGS. 1-3) and the second position 42 is substantially other than perpendicular to the longitudinal axis 36 (same as in the embodiment shown in FIG. 6). The at least one flap 22 may be adapted to move between the first and second positions in response to contact by a blood component, for example a blood cell.

Further, as can be seen from the figures, the apparatus 54 may include multiple sets of these flaps. Thus, in certain embodiments, such as the illustrated embodiment, the plurality of flaps 38 includes multiple subsets of flaps, each subset of flaps including at least one flap. Thus, at a minimum, the multiple subsets of flaps includes at least a first subset 44 and a second subset 46 spaced apart from one another along the body 12 of the apparatus.

In one embodiment, each of the plurality of flaps 38 may be coplanar with each of the other flaps of the plurality of flaps. Thus, a plurality of flaps 38 may be spaced equidistant from one another and in the same plane around the circumference of the cylindrical side wall 14 of the illustrated embodiment. However, as will be apparent to those of ordinary skill in the art, it is not necessary that the flaps that lie in the same plane be equidistant from one another about the interior surface of the side wall.

Additionally or alternatively, the plurality of flaps 38 may include at least a first subset 44 of flaps and a second subset 46 of flaps. In such an embodiment, each flap 22 of the first subset 44 of flaps is coplanar with each of the other flaps of the first subset 44 of flaps along a first plane, and each flap 22 of the second subset 46 of flaps is coplanar with each of the other flaps of the second subset 46 of flaps along a second plane, with the second plane not being coplanar with the first plane. There may be additional (i.e., third, fourth, fifth) subsets of flaps that each lie in their own planes, which are separate from the first and second planes.

Further, as described above, the apparatus 54 includes at least one groove 24 disposed in a surface of the at least one flap. The groove 24 or grooves can be seen at least in FIGS. 5-7. Further, in embodiments including a plurality of flaps 38 and/or multiple subsets of pluralities of flaps, the flaps may include one groove 24 on each flap, more than one groove 24 on each flap, or differing numbers of grooves on each flap 22 (as compared to the number of grooves on other flaps). Further, certain flaps of the plurality of flaps 38 may have no grooves at all. The grooves are cut at an angle, such that they scoop any virus 30 on the surface of the cell, trapping the virus 30 in the groove 24 as the blood cell 26 passes through. When the flap 22 returns to its normal position, the gap in the grooves would no longer be at an expanded size, crushing the virus 30 in the groove. Thus, the size of the groove 24 will be cut smaller than the virus 30 one desires to treat.

Further, the at least one groove 24 moves between a non-expanded condition 50 and an expanded condition 52 as the at least one flap 22 moves between first and second positions. Thus, in one exemplary embodiment, the at least one groove 24 is in the non-expanded condition 50 when the at least one flap 22 is in the first position 40 (See FIG. 5), and the at least one groove 24 is in the expanded condition 52 when the at least one flap 22 is in the second position 42 (See FIG. 6). As such, the at least one groove 24 is sized larger than a virus 30 the apparatus 54 is adapted to reduce, when the at least one groove 24 is in the expanded condition. And, the at least one groove 24 is sized smaller than a virus 30 the apparatus 54 is adapted to reduce, when the at least one groove 24 is in the non-expanded condition.

The apparatus 54 is used such that blood is caused to flow through the interior space 16 of the body, from one of the first and second ends to the other of the first and second ends. The blood may be from a subject infected with a virus, such that the blood includes cells infected with viruses. As blood passes through the body, the at least one flap 22 contacts and rubs the outer surface of a blood cell, which bends the at least one flap 22 back the direction of the blood flow. As this occurs, the size of the at least groove 24 on the surface of the at least one flap 22 increases (due to the malleable material of the flap 22 or flaps) the groove 24 or grooves are cut at an angle, such that they scoop any virus 30 on the surface of the cell, trapping the virus 30 in the groove 24 as the blood cell 26 passes through the interior space.

Once the cell 26 is no longer in contact with the flap, the flap 22 returns to its normal position, and the width of the grooves return to their non-expanded size, thereby crushing the virus 30 in the groove. In order to crush the virus 30 (and render it inert), the width of the groove 24 will be cut smaller than the width of the virus 30 one desires to reduce/eliminate. For example, if the virus 30 has a width of 120 nm, grooves could be cut with a nonexpanded width less than 120 nm (for example, at 80 nm to 90 nm) to insure that the virus 30 is crushed, so genetic material escapes the capsid and is rendered inert. While the groove 24 is cut at a non-expanded width that is smaller than the width of the virus 30 to be reduced/eliminated, the width of the groove 24 is also such that it can expand to at least the width of the virus 30 (in the example above, 120 nm), or more. Each flap 22 may also include multiple grooves, including grooves of different widths.

The embodiments of the present invention recited herein are intended to be merely exemplary and those skilled in the art will be able to make numerous variations and modifications to it without departing from the spirit of the present invention. Notwithstanding the above, certain variations and modifications, while producing less than optimal results, may still produce satisfactory results. All such variations and modifications are intended to be within the scope of the present invention as defined by the claims appended hereto.

What is claimed is:

1. An anti-viral device comprising:

a body having at least one side wall defining an interior space therein, the body having opposite first and second ends, said first and second ends also defined by the at least one side wall and said first and second ends being in fluid communication with the interior space;

at least one flap associated with said at least one side wall and extending into the interior space from the at least one sidewall, the at least one flap being flexible and adapted to move between first and second positions; and at least one groove disposed in a surface of the at least one flap;

wherein the at least one groove moves between a non-expanded condition and an expanded condition as the at least one flap moves between the first and second positions;

wherein the at least one groove is sized larger than a virus the device is adapted to reduce, when the at least one groove is in the expanded condition, and wherein the at least one groove is sized smaller than a virus the device is adapted to reduce, when the at least one groove is in the non-expanded condition.

2. The anti-viral device of claim 1, wherein the at least one side wall is chosen from an open framework and a solid wall.

3. The anti-viral device of claim 1, wherein the at least one flap is continuous about an inner surface of the at least one side wall.

4. The anti-viral device of claim 1, wherein the at least one flap is a member of a plurality of flaps.

5. The anti-viral device of claim 4, wherein each flap of the plurality of flaps extends into the interior space from the at least one sidewall, each flap of the plurality of flaps being flexible.

6. The anti-viral device of claim 1, wherein the at least one groove is a member of a plurality of grooves, each groove of the plurality of grooves being disposed in a surface of a flap of the plurality of flaps.

7. The anti-viral device of claim 1, wherein the first position is substantially perpendicular to a longitudinal axis of the body and the second position is substantially other than perpendicular to the longitudinal axis of the body.

8. The anti-viral device of claim 1, wherein the at least one flap is adapted to move between first and second positions in response to contact by a blood cell.

9. The anti-viral device of claim 5, wherein the plurality of flaps includes multiple subsets of flaps, each subset including at least one flap.

10. The anti-viral device of claim 9, wherein the multiple subsets of flaps includes at least a first subset and a second subset spaced apart from one another along the body.

11. The anti-viral device of claim 1, wherein the at least one groove is disposed in the at least one flap at an angle that is other than orthogonal to the longitudinal axis of the at least one flap.

12. The anti-viral device of claim 1, wherein the at least one groove is in the non-expanded condition when the at least one flap is in the first position, and wherein the at least one groove is in the expanded condition when the at least one flap is in the second position.

13. An anti-viral apparatus comprising:

a housing having a conduit for the passage of fluids defined therein, the conduit including an interior space;

at least one flap associated with said conduit and extending into the interior space, the at least one flap being flexible and adapted to move between first and second positions; and at least one groove disposed in a surface of the at least one flap;

wherein the at least one groove moves between a non-expanded condition and an expanded condition as the at least one flap moves between first and second positions; and wherein the at least one groove is sized larger than a virus the apparatus is adapted to reduce, when the at least one groove is in the expanded condition, and wherein the at least one groove is sized smaller than a virus the apparatus is adapted to reduce, when the at least one groove is in the non-expanded condition.

14. The anti-viral apparatus of claim 13, wherein the at least one flap is a member of a plurality of flaps, each flap of the plurality of flaps extending into the interior space toward the longitudinal axis of the conduit, each flap of the plurality of flaps being flexible.

15. The anti-viral apparatus of claim 14, wherein the at least one groove is a member of a plurality of grooves, each groove of the plurality of grooves being disposed in a surface of a flap of the plurality of flaps.

16. The anti-viral apparatus of claim 13, wherein the at least one flap is adapted to move between first and second positions, the first position being substantially perpendicular to a longitudinal axis of the body and the second position being substantially other than perpendicular to the longitudinal axis of the body.

17. The anti-viral apparatus of claim 14, wherein the plurality of flaps includes at least a first subset of flaps and a second subset of flaps spaced apart from one another along the conduit.

18. An anti-viral apparatus comprising:

a housing having a conduit for the passage of fluids defined therein, the conduit including an interior space;

at least one flap associated with said conduit and extending into the interior space, the at least one flap being flexible, wherein the at least one flap is adapted to move between first and second positions, the first position being substantially perpendicular to a longitudinal axis of the body and the second position being substantially other than perpendicular to the longitudinal axis of the body; and at least one groove disposed in a surface of the at least one flap;

wherein the conduit allows for the passage of fluids through the housing when the at least one flap is in the first position and when the at least one flap is in the second position wherein the at least one groove moves between a non-expanded condition and an expanded condition as the at least one flap moves between the first and second positions;

wherein the at least one groove is sized larger than a virus the device is adapted to reduce, when the at least one groove is in the expanded condition, and wherein the at least one groove is sized smaller than a virus the device is adapted to reduce, when the at least one groove is in the non-expanded condition.

* * *

UNITED STATES PATENT AND TRADEMARK OFFICE
CERTIFICATE OF CORRECTION

PATENT NO.         : 8,556,085 B2                                      Page 1 of 1
APPLICATION NO.    : 12/941137
DATED              : October 15, 2013
INVENTOR(S)        : Stuart Bogle It is certified that error appears in the above-identified patent and that said Letters Patent is hereby corrected as shown below:

In the Specification
Column 2,
Line 12 reads "the length of" and should read --of the length of--.

Column 10,
Line 18 reads "(See FIG. 5)," and should read --(see FIG. 5),--.
Lines 20-21 read "(See FIG. 6)." and should read --(see FIG. 6).--.

Column 12,
Line 38 reads "(See FIG. 5)," and should read --(see FIG. 5),--.
Line 40 reads "(See FIG. 6)." and should read --(see FIG. 5).--.

Signed and Sealed this
Third Day of June, 2014

Michelle K. Lee
*Deputy Director of the United States Patent and Trademark Office*

UNITED STATES PATENT AND TRADEMARK OFFICE
CERTIFICATE OF CORRECTION

Page 1 of 1

PATENT NO. : 8,556,085 B2
APPLICATION NO. : 12/941137
DATED : October 15, 2013
INVENTOR(S) : Stuart Bogle It is certified that error appears in the above-identified patent and that said Letters Patent is hereby corrected as shown below:

In the Specification
Column 2,
Line 12 reads "the length of" and should read --of the length of--.

Column 10,
Line 18 reads "(See FIG. 5)," and should read --(see FIG. 5),--.
Lines 20-21 read "(See FIG. 6)." and should read --(see FIG. 6).--.

Column 12,
Line 38 reads "(See FIG. 5)," and should read --(see FIG. 5),--.
Line 40 reads "(See FIG. 6)." and should read --(see FIG. 6).--.

This certificate supersedes the Certificate of Correction issued June 3, 2014.

Signed and Sealed this
Ninth Day of September, 2014

Michelle K. Lee
*Deputy Director of the United States Patent and Trademark Office*